US010449980B1

(12) United States Patent
Sivaswamy

(10) Patent No.: US 10,449,980 B1
(45) Date of Patent: Oct. 22, 2019

(54) PROVIDING AN ALERT TO A PASSENGER BASED ON A LOCATION OF THE PASSENGER WHILE IN TRANSIT ON A MULTI-PASSENGER MODE OF TRANSPORT

(71) Applicant: International Business Machines Corporation, Armonk, NY (US)

(72) Inventor: Hemant K. Sivaswamy, Pune (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/968,970

(22) Filed: May 2, 2018

(51) Int. Cl.
| G08B 5/36 | (2006.01) |
| B61K 13/00 | (2006.01) |
| G01G 19/08 | (2006.01) |
| G01G 19/50 | (2006.01) |
| A61B 5/1174 | (2016.01) |
| G06K 9/00 | (2006.01) |

(52) U.S. Cl.
CPC ............ *B61K 13/00* (2013.01); *A61B 5/1174* (2013.01); *G01G 19/08* (2013.01); *G01G 19/50* (2013.01); *G08B 5/36* (2013.01); *G06K 9/00885* (2013.01)

(58) Field of Classification Search
CPC ...... B61K 13/00; A61B 5/1174; G01G 19/08; G01G 19/50; G08B 5/36; G06K 9/00885

USPC ...................................................... 340/686.6
See application file for complete search history.

(56) References Cited

U.S. PATENT DOCUMENTS

| 6,374,176 B1* | 4/2002 | Schmier ................ G08G 1/123 340/988 |
| 7,233,240 B2* | 6/2007 | Phillips ................ G08G 1/123 340/539.13 |
| 2007/0069021 A1 | 3/2007 | Elrod et al. |
| 2008/0195257 A1* | 8/2008 | Rauch ...................... B61B 1/02 701/1 |
| 2009/0115610 A1 | 5/2009 | Steinhage et al. |
| 2017/0213165 A1* | 7/2017 | Stauffer ............... G06Q 10/02 |
| 2017/0252256 A1 | 9/2017 | Henshue et al. |
| 2018/0190126 A1* | 7/2018 | Teslenko ............... G07B 15/02 |
| 2019/0124619 A1* | 4/2019 | Arumugam ........ G06Q 30/0205 |

* cited by examiner

*Primary Examiner* — Nay Tun
(74) *Attorney, Agent, or Firm* — Cuenot, Forsythe & Kim, LLC

(57) ABSTRACT

Providing an alert to a user of a multi-passenger mode of transport includes receiving first biometric information about the user and a destination for the user; receiving second biometric information about the user; based on the second biometric information, determining the destination for the user; based at least in part on the destination for the user, determining a first location within the multi-passenger mode of transport; and transmitting a first command to control a first display device proximate to the user, based on the first location.

20 Claims, 9 Drawing Sheets

US 10,449,980 B1

PROVIDING AN ALERT TO A PASSENGER BASED ON A LOCATION OF THE PASSENGER WHILE IN TRANSIT ON A MULTI-PASSENGER MODE OF TRANSPORT

BACKGROUND

The present invention relates to multi-passenger modes of transport, and more specifically, to the ingress and egress of passengers for multi-passenger modes of transport.

Multi-passenger modes of transport, such as trains or busses, allow for efficient and economical movement of large numbers of people as opposed to other types of vehicles such as automobiles. However, when a passenger enters the train, for example, they may stand close to the door even though their destination is farther away than the destination of another passenger that is standing farther from the door. Thus, when the other passenger tries to disembark, they may have difficulty getting to and out the door.

SUMMARY

A method includes receiving, by a processor, first biometric information about a user of a multi-passenger mode of transport and a destination for the user; receiving, by the processor, second biometric information about the user; based on the second biometric information, determining, by the processor, the destination for the user; based at least in part on the destination for the user, determining, by the processor, a first location within the multi-passenger mode of transport; and transmitting, by the processor, a first command to control a first display device proximate to the user, based on the first location.

A system includes a processor programmed to initiate executable operations. The executable operations include receiving first biometric information about a user of a multi-passenger mode of transport and a destination for the user; receiving second biometric information about the user; based on the second biometric information, determining the destination for the user; based at least in part on the destination for the user, determining a first location within the multi-passenger mode of transport; and transmitting a first command to control a first display device proximate to the user, based on the first location.

A computer program product includes a computer readable storage medium having program code stored thereon. The program code is executable by a data processing system to initiate operations. The operations include receiving, by the data processing system, first biometric information about a user of a multi-passenger mode of transport and a destination for the user; receiving, by the data processing system, second biometric information about the user; based on the second biometric information, determining, by the data processing system, the destination for the user; based at least in part on the destination for the user, determining, by the data processing system, a first location within the multi-passenger mode of transport; and transmitting, by the data processing system, a first command to control a first display device proximate to the user, based on the first location.

DETAILED DESCRIPTION

As defined herein, the term "responsive to" means responding or reacting readily to an action or event. Thus, if a second action is performed "responsive to" a first action, there is a causal relationship between an occurrence of the first action and an occurrence of the second action, and the term "responsive to" indicates such causal relationship.

As defined herein, the term "computer readable storage medium" means a storage medium that contains or stores program code for use by or in connection with an instruction execution system, apparatus, or device. As defined herein, a "computer readable storage medium" is not a transitory, propagating signal per se.

As defined herein, the term "data processing system" means one or more hardware systems configured to process data, each hardware system including at least one processor programmed to initiate executable operations and memory.

As defined herein, the term "processor" means at least one hardware circuit (e.g., an integrated circuit) configured to carry out instructions contained in program code. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "automatically" means without user intervention.

As defined herein, the term "user" means a person (i.e., a human being).

Figure 1:
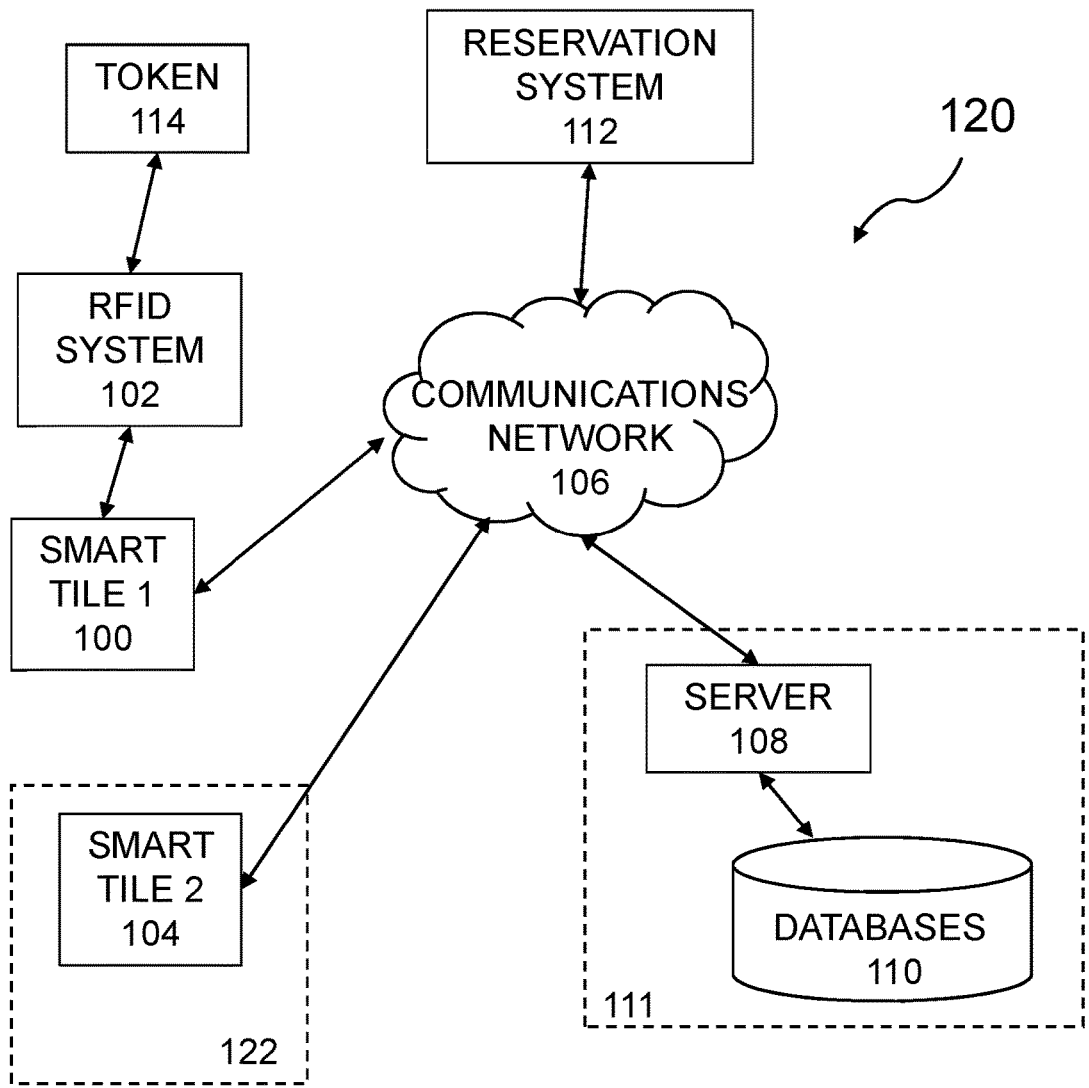
FIG. 1 is a block diagram illustrating an example of a network data processing system in accordance with the principles of the present disclosure.

FIG. 1 is a block diagram illustrating an example of a network data processing system 120 that includes a communication network 106. The communication network 106 is the medium used to provide communications links between various devices and data processing systems connected together within the computing environment (or network data processing system, etc.) 120. The communication network 106 may include connections, such as wire, wireless communication links, or fiber optic cables. The communication network 106 can be implemented as, or include, any of a variety of different communication technologies such as a wide area network (WAN), a local area network (LAN), a wireless network, a mobile network, a Virtual Private Network (VPN), the Internet, the Public Switched Telephone Network (PSTN), or similar technologies.

One device in the network data processing system 120 is a first smart tile 100. As explained in more detail below with respect to FIG. 4, the smart tile 100 collets biometric data about a user, or passenger, such as a footprint outline or a weight. The smart tile 100 can also interrogate a NFC device (e.g., an RFID token 114) when that NFC device is within a certain proximity of the smart tile 100. The threshold proximity is based on the specific NFC technology being used but typically can range from a few millimeters (e.g., 1-10) to a few meters (e.g., 1-5). Additionally, the smart tile 100 can communicate with the network 106 to transmit and receive information from other connected devices.

A second smart tile 104 is shown in FIG. 1. This smart tile is substantially similar to the other smart tile 100 in terms of functions and features. However, the second smart tile 104 is located at a different geographical location than the first smart tile 100. In particular, the second smart tile 104 can be located within the body of a multi-passenger mode of transport 122. Such a mode of transport 122 can include, for example, a train car, a bus, a boat compartment, a subway car, etc. For purposes of clarity and conciseness, an example environment, described herein will include a train car for which a passenger is provided with an RFID token that is read by an RFID reader located near a turnstile through which the passenger must pass to reach a platform to board the train car. One of ordinary skill will recognize that, within the scope of the present disclosure, NFC technologies other than RFID may be used, multi-passenger modes of transport other than trains may be used, and access barriers other than turnstiles may be used.

Generally, many devices have long been presumed to be heterogeneous with respect to each other, such as desktop devices, mobile communicators, digital assistants, wrist watches, game consoles, clothing, consumer electronics (e.g., TVs, radios, and refrigerators), cars, sensors, smart meters, and video surveillance equipment, to name but a few examples. However, advancements in the realm of networking, sensors, actuators, radio frequency identification (RFID) and other near field communication (NFC) technologies have made it possible to connect various devices and real-world objects and or virtual objects which have been labeled as the Internet of Things (IoT). In accordance with embodiments herein, the smart tiles 204 are an example of such devices that collect data about their physical environment and communicate with other objects.

A reservation system 112 may be part of the system 120 and allows a passenger to book a travel itinerary that includes at least a departure location and a destination location. Prior to arriving at the departure location, or once the passenger arrives at the departure location, the passenger can receive a token that electronically stores the itinerary information.

In contrast to the location of the second smart tile 104, the first smart tile 100 can be located near an RFID system 102 that is able to read data stored on the token 114. The token 114 may be an RFID token that includes itinerary information about the passenger and the RFID system 102 can be part of a turnstile through which the passenger must pass to gain access to a platform, or other location, to board the train car 122.

A central system 111 can include a server 108 and its accompanying data store 110 and can communicate with the smart tiles 100, 104. As explained in detail below, the system 111 receives biometric information about a passenger (e.g., weight, footprint outline, etc.), along with destination information, from the first smart tile 100. The system 111 also receives biometric information from the second smart tile 104 about a nearby user who is in transit on the train car 122. Based on the biometric information received from the second smart tile 104, the system 111 identifies a matching set of biometric information received from the first smart tile 100. The system 111 then determines the destination information associated with the identified matching biometric information. Based on the location of the second smart tile 104 from an entrance to the train car 122 and the destination, the system 111 determines where in the train car 122 the passenger should stand or sit. The system 111 can then transmit a command to the second smart tile 104 instructing the smart tile 104 to control a display device that is nearby. The display device can, for example, be a portion of a top surface of the second smart tile 104 and can be instructed to emit light of a certain color based on the command.

Figure 2A:
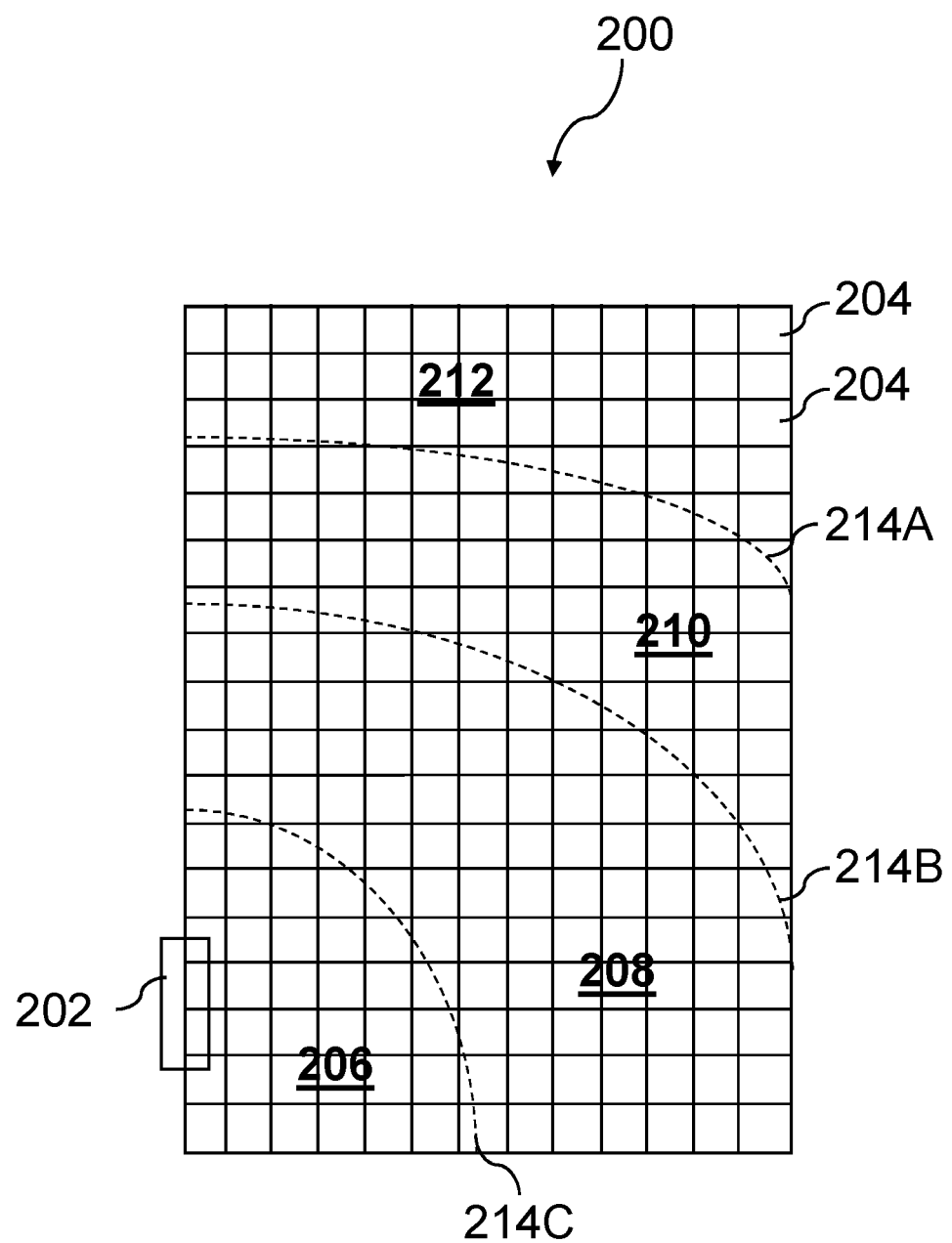
FIGS. 2A-2C are plan views illustrating example architectures for a multi-passenger mode of transport in accordance with the principles of the present disclosure.
Figure 2B:
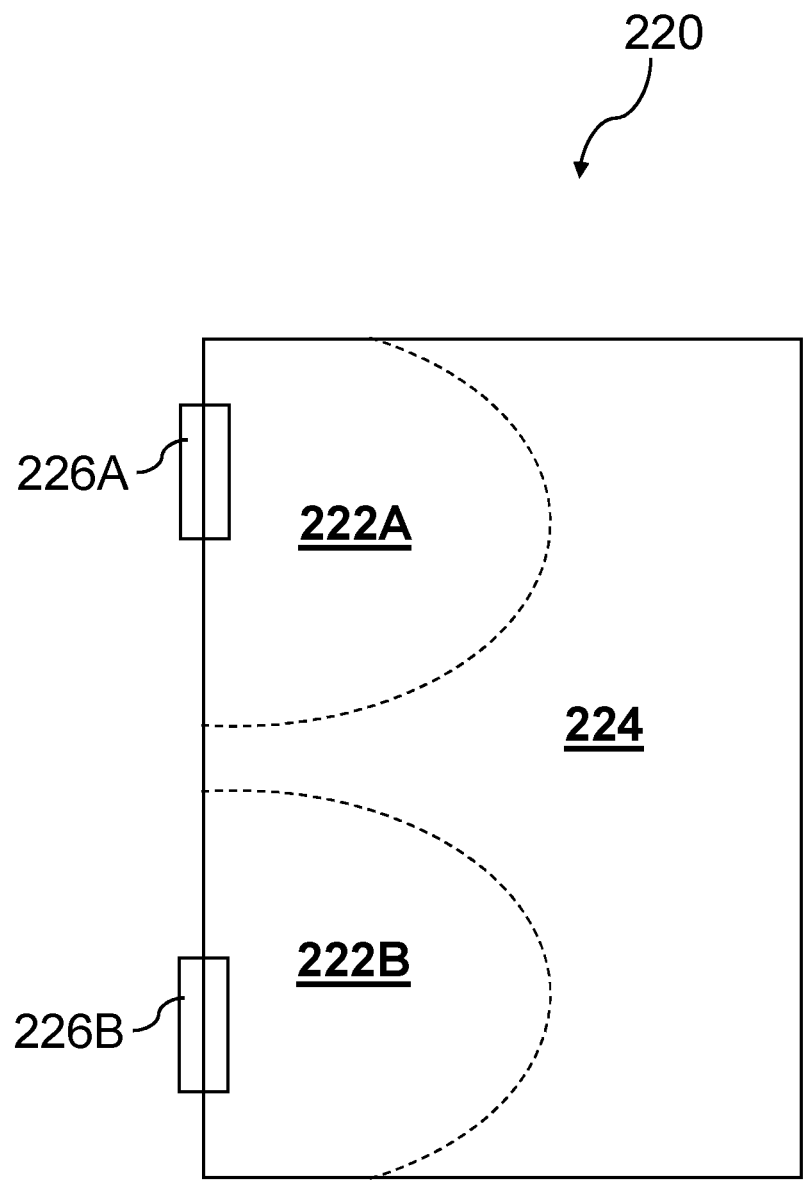
Figure 2C:
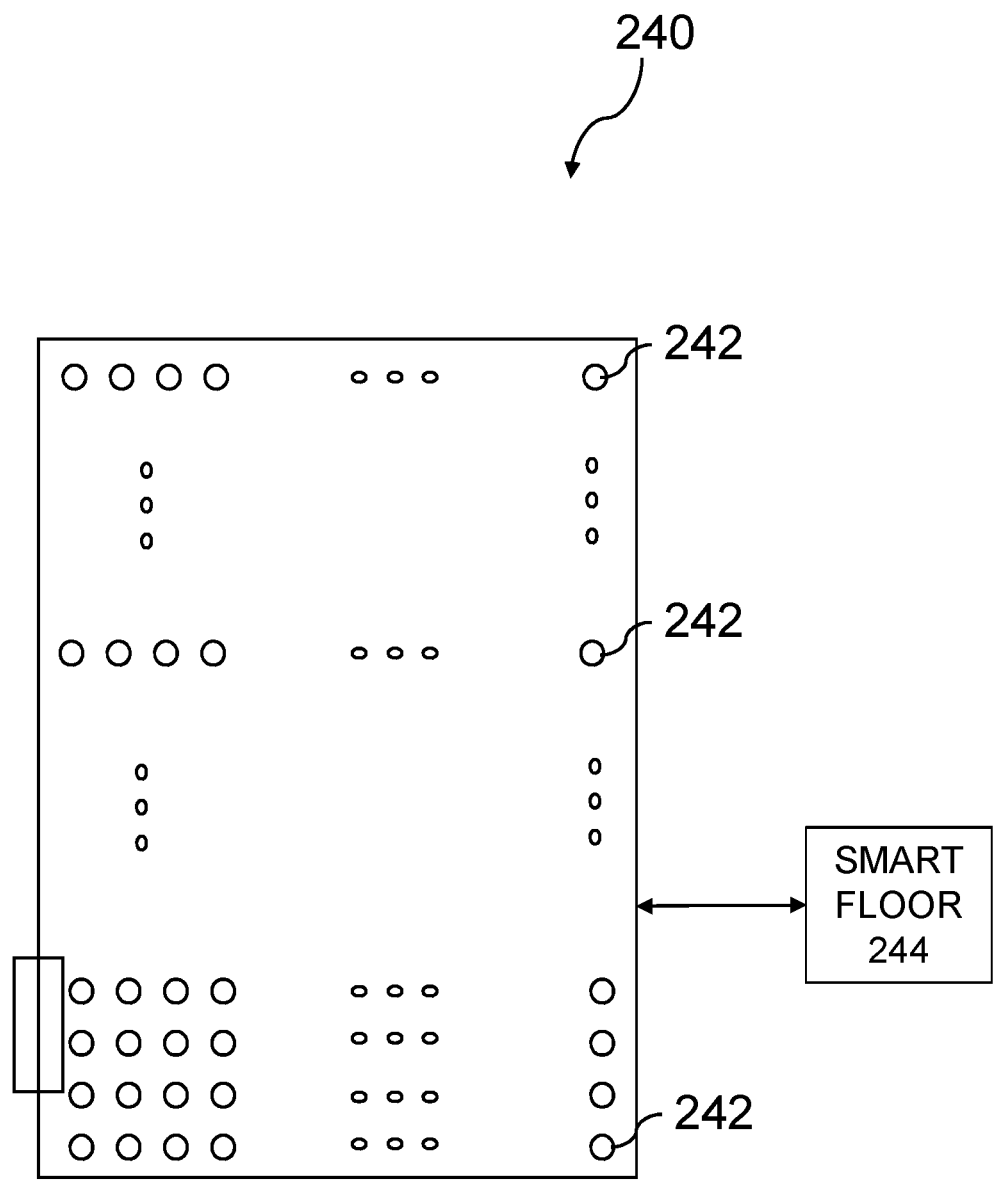

FIGS. 2A-2C are plan views illustrating example architectures for a multi-passenger mode of transport in accordance with the principles of the present disclosure. In FIG. 2A, a train car 200 has an access point 202 (e.g., a doorway or other opening) and its floor surface is covered with smart tiles 204. One of ordinary skill can appreciate that there may be benches or chairs (not shown) within the train car 200 and smart tiles 204 can be eliminated in those locations. Smart tiles 204 are examples of the second smart tile 104 discussed above with respect to claim 1.

Imaginary boundaries 214A, 214B, and 214C separate the floor of the train car 200 into sections 206, 208, 210 and 212 (also referred to herein as "zones" or "regions"). Each of the sections define a respective region of the train car that is progressively farther from the access point 202. In other words, region 208 is farther from the access point 202 than region 206, region 210 is farther from the access point 202 than region 208 and region 212 is farther from the access point 202 than region 210. For those smart tiles 204 that are located at one of the boundaries 214A, 214B, 214C, they can be defined as part of one of the two regions that they overlap according to predetermined rules (e.g., assigned to the region in which a majority surface area of that smart tile is located.

In its simplest embodiment, the train car 200 can have a single imaginary boundary that separates the smart tiles 204 into two different regions. When a passenger enters the train car 200 and stops on one of the smart tiles 204, that smart tile communicates with the central system 111 to determine whether or not the location of the smart tile is appropriate based on the intended destination of the passenger. If the passenger's destination location is relatively far from the embarking location, then the passenger should locate themselves far from the access point 202. If, however, the destination location is nearby, then the passenger should locate themselves close to the access point 202. If the passenger has stopped on a smart tile located in the appropriate region of the train car, then the smart tile can emit a certain color (e.g., green). If the passenger has not stopped in the appropriate region then the smart tile can emit a different color (e.g., red).

In an embodiment, as is shown in FIG. 2A, in which there are more than two regions defined in the train car 200, a convention could be defined such that the smart tiles emit "red" in any region that is not far enough from the access point but emit "green" for the region appropriate for the passenger and for any region that is farther still from the access point 202.

The determination by the system 111 on the appropriate region for a passenger can be based on the distance, from the access point 202, the smart tiles in a region are and the number of stops until the intended destination of the passenger. For example, all passengers disembarking at the next stop, or the next x stops, should be located in the region closest to the access point 202. The other passengers should be located in a different region that is farther from the access point 202. In order to make this determination, the central system 111 uses knowledge about where each smart tile 204 is located relative to the access point. This knowledge can be transmitted by the smart tile 204 to the system 111 based on information stored within the smart tile 204, or the distance information can be associated with a smart tile identifier (e.g., an IP address) and pre-programmed in the central system 111. Thus, when a smart tile 204 communicates with the central system 111, that system can determine the location of the smart tile 204 relative to the access point 202.

FIG. 2B illustrates an example train car 220 that has two access points 226A, 226B. The imaginary boundaries utilized in this example take into account both access points 226A, 226B and define two regions 222A, 222B that are closer to an access point that a third region 224.

In FIG. 2A, each smart tile 204 is sized to be larger than an average passenger's foot size (e.g., one foot). As long as a passenger stands with a foot fully on a smart tile 204, their appropriate region within the train car 200 can be determined. An alternative sensor arrangement is depicted in which the floor includes a plurality of sensors 242 that are located with a spacing closer than one foot (e.g., 3 to 6 inches) or even closer (less than one inch). The sensor data from the sensors 242 is organized into multiple detected footprints and weights wherein each pair of a footprint and a weight correspond to one passenger.

One way to organize the sensor data is to first analyze all the sensor data to determine distinct footprint outlines and then group the sensors located within each distinct footprint outline into a respective set. The weight measured for each of the sensors in a set is then determined to define a footprint/weight pair. Instead of multiple smart tiles 204 communicating with the central system 111, the train car 240 of FIG. 2C has a smart floor 244 that communicates with the central system 111 in order to transmit all of the different passenger information to the system 111. The determination of identifying matching biometric data and determining an appropriate location for a particular passenger remains much the same as discussed with respect to FIGS. 2A and 2B. In this instance, however, the smart floor 244 keeps track of the multiple passenger locations so that it can translate commands received from the central system 111 into instructions for the different regions of the floor so as to control them to emit an appropriate color.

The sensors 242 can, for example, be a multitude of pressure sensors that are each coupled with a pin or similar structure. The top surface of the floor can be constructed to be slightly deformable when a passenger steps or stands on the floor. The pins can be located between the underside of the floor's top surface and the sensors such that a passenger standing on a section of the floor would cause a number of the pins to push down onto a respective pressure sensor. A contiguous set of pressure sensors that detect pressure from above would be considered a footprint and this set of sensors would define the outline or shape of the footprint. The pressure sensors can also determine a weight of the passenger that is associated with the footprint. A multicolor LED can be associated with each of the pressure sensors, as well. Once the smart floor 244 receives an identification of the destination associated with the passenger, the smart floor 244 can be instructed to cause the LEDs near the outside edges of the footprint to glow a particular color based on the distance from the footprint to a closest door of the train car.

Figure 3:
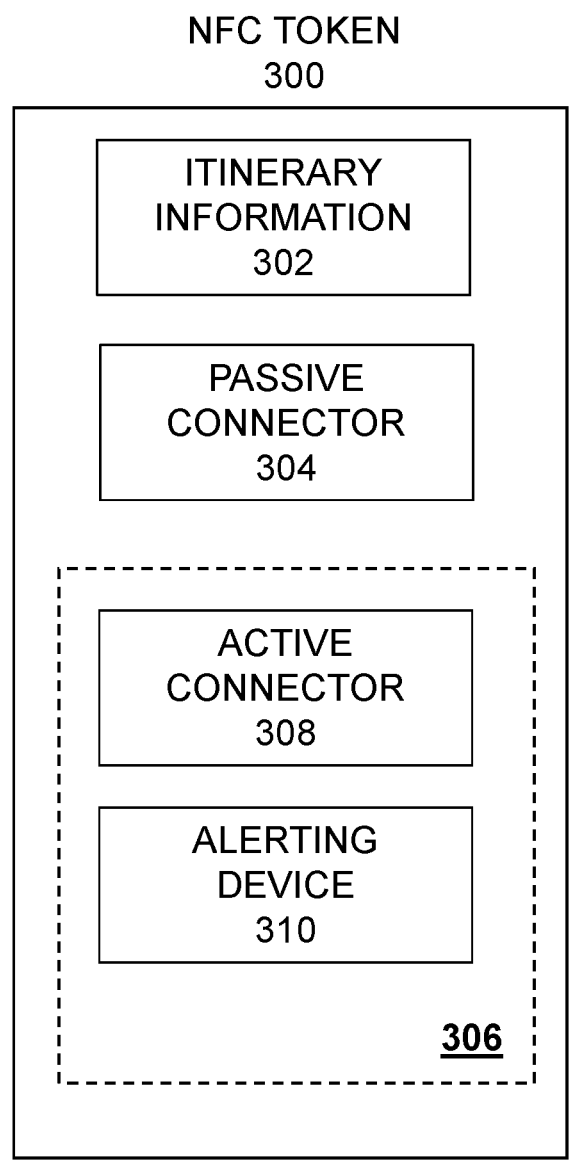
FIG. 3 is a block diagram illustrating an example near field communication (NFC) token in accordance with the principles of the present disclosure.

FIG. 3 is a block diagram illustrating an example near field communication (NFC) token in accordance with the principles of the present disclosure. The token 300 can be a relatively simple, passive RFID token that stores the passenger itinerary information 302. As one example, when a passenger buys a ticket for the train, or redeems a ticket bought previously, the appropriate personnel of the rail system can program the token 300 with the passenger's itinerary information 300 and then give the token 300 to the passenger. The token 300 also, at the least, includes a passive connector 304. For example, the passive connector 304 can be a passive antenna which can be interrogated by a token reader. When the token 300 is interrogated, the reader can receive the itinerary information 302 from the token 300. The itinerary information, at the very least, includes a destination at which the passenger intends to disembark from the train.

In some embodiments, the token 300 can also include optional capabilities 306 such as an active connector (e.g., a radio transceiver) 308 and an alerting device 310. Other sensors (not shown) can be included as well. As one example, the alerting device 310 may vibrate, or flash, or make an audible sound when the passenger is within one or two stops from their destination. The nearby smart tile can inform the token 300 that the destination is approaching, or the token could include GPS or other, similar capability to independently determine that the destination is approaching. In one alternative, one or more of the smart tiles can be controlled so as to vary their visual display properties based on a passenger approach their destination. The smart tile on which the passenger is standing may change color (e.g., change to blue) to indicate to the user that their destination is approaching and they should consider moving closer to the access point. The smart tile may instead blink and can remain the same color to try to alert the passenger. Another alternative would be for the smart tile to blink and the one or more adjacent smart tiles in the direction of the access point to change color or other wise change visually. Thus, the smart tile is periodically monitoring the passenger to discover that the passenger remains standing on the smart tile even though their stop is approaching soon. The passenger may then be alerted so that they can begin moving closer to the access point of the train car.

The alerting device 310 can also be utilized to indicate to the passenger that they should move farther from the door of the train car based on their intended destination. Thus, instead of a smart tile glowing red or green, or portions of a smart floor glowing red or green, an LED or similar indicator that is part of the token 300 can glow read or green. In this way, the passenger does not have to look down towards their feet to determine if they are at a desired location in the train car. Instead, by simply observing the token 300, the passenger can identify when the alerting device 310 changes from red to green.

Figure 4:
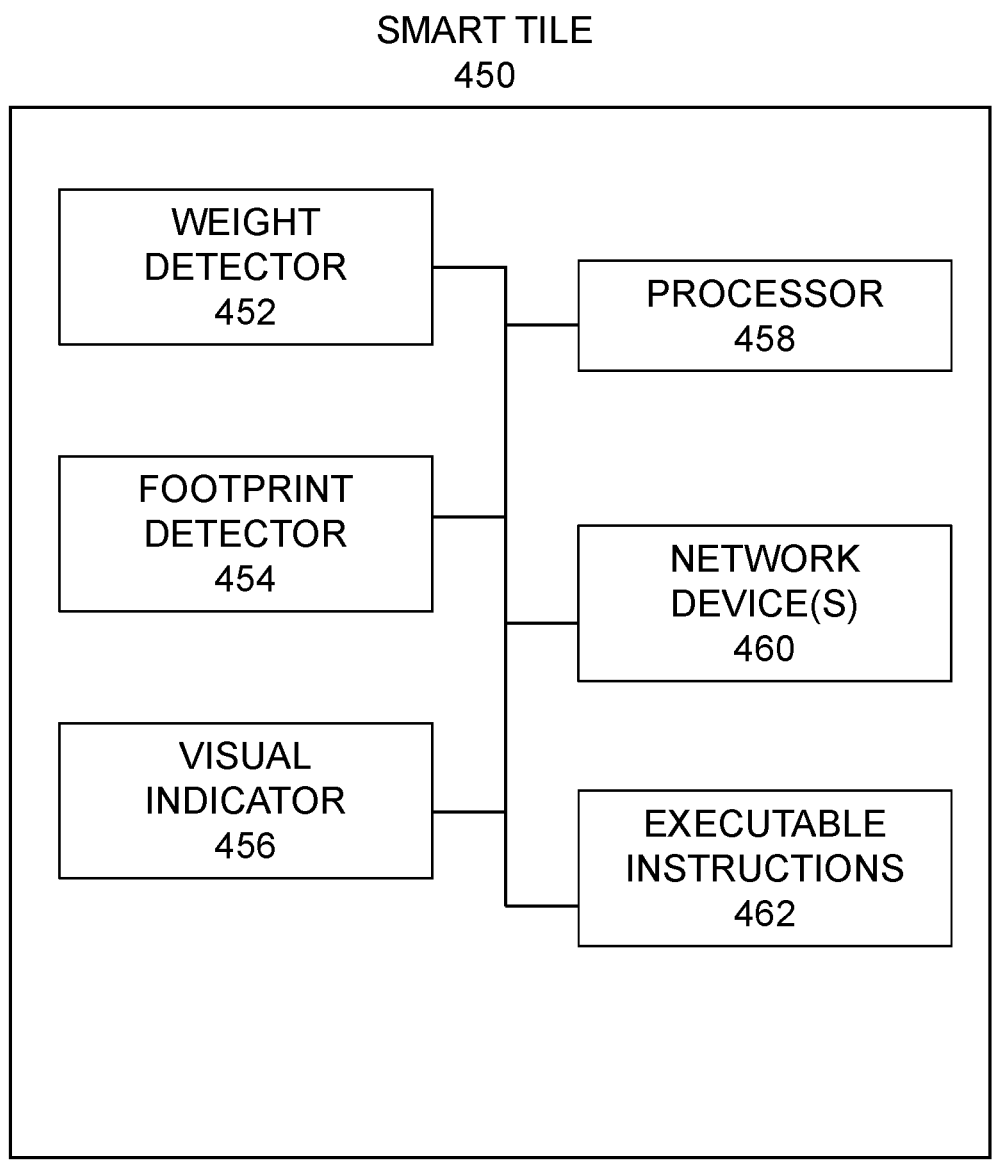
FIG. 4 is a block diagram illustrating an example smart tile in accordance with the principles of the present disclosure.

FIG. 4 is a block diagram illustrating an example smart tile in accordance with the principles of the present disclosure. The smart tile 450 includes a weight detector 452, a footprint detector 454, a visual indicator 456, a processor 458 and a network device 460. The processor 458 executes instructions 462 to coordinate and control the activities of the other elements of the smart tile 450. The network device 460 communicates to and from the central system 111 and the other elements 452, 454, 456, 458 of the smart tile 450. The network device 460 can also include communication elements that allow it to interrogate a NFC communication token such as token 300 described above in order to determine information stored by the token. In additional embodiments, the network device can be sophisticated enough to provide two-way transmission of data with a token using various NFC technologies.

The smart tile 450 can, in one example, be between 12 to 18 inches square and designed to be assembled into a floor on which people walk or stand. The surface material is selected to be durable enough to withstand expected foot traffic and various sensors and circuitry are embedded below the surface within the smart tile.

One of ordinary skill will recognize that the weight detector 452 can be any of a number of typical transducers that measure the weight of an object, without departing from the scope of the present disclosure. The footprint detector 454 can also be selected from a variety of different sensors or transducers. One type of sensor may include multiple LEDs that emit light (visible and/or non-visible) that is reflected back by the sole of a passenger's shoe and detected by a plurality of detectors, each co-located with one of the LEDs. One alternative could be to use a plurality of photodetectors that receive ambient light such that a detector below the sole of a passenger's shoe would not receive such light. Other sensors can include an ultrasound proximity detector, capacitive touch detection or pressure transducers to determine an outline of the sole of a passenger's foot standing on the top surface of a smart tile. For the smart floor example of FIG. 2C, there would be a pair of sensors consisting of a weight sensor and a footprint detector. There would be a plurality of these sets (each sensor pair depicted as element 242 in FIG. 2C) and the processor of the smart floor 242 would know the location of each set of sensors.

The visual indicator 456 can be a portion of the smart tile 450 that emits a visual cue or alert for the passenger. As described in one example above, the visual indicator 456 may emit red light to alert the passenger that they should move to a location farther from the access point bur emit green light when the passenger is in an appropriate location. The visual indicator 456 may be one or more LEDs under the surface of the smart tile 450 such that the light is diffused by the top surface to create the effect that the entire smart tile is glowing red or green. Alternatively, one or more LEDs or other of light emitters could be located around the smart tile 450 so that only portions of the smart tile 456 appear to be glowing a certain color. For the smart floor example of FIG. 2C, each of the sensor sets 242 can also include an associated LED. Because the smart floor 244 has determined the footprint outline, the smart floor also can identify the sensor sets 242 which are located closest to the footprint outline edges. The respective LEDs associated with one or more of the identified sensor sets 242 could be controlled by the smart floor 244 to emit light. In this way, the top surface of the floor in close proximity to the passenger's foot would glow in a particular color.

Figure 5A:
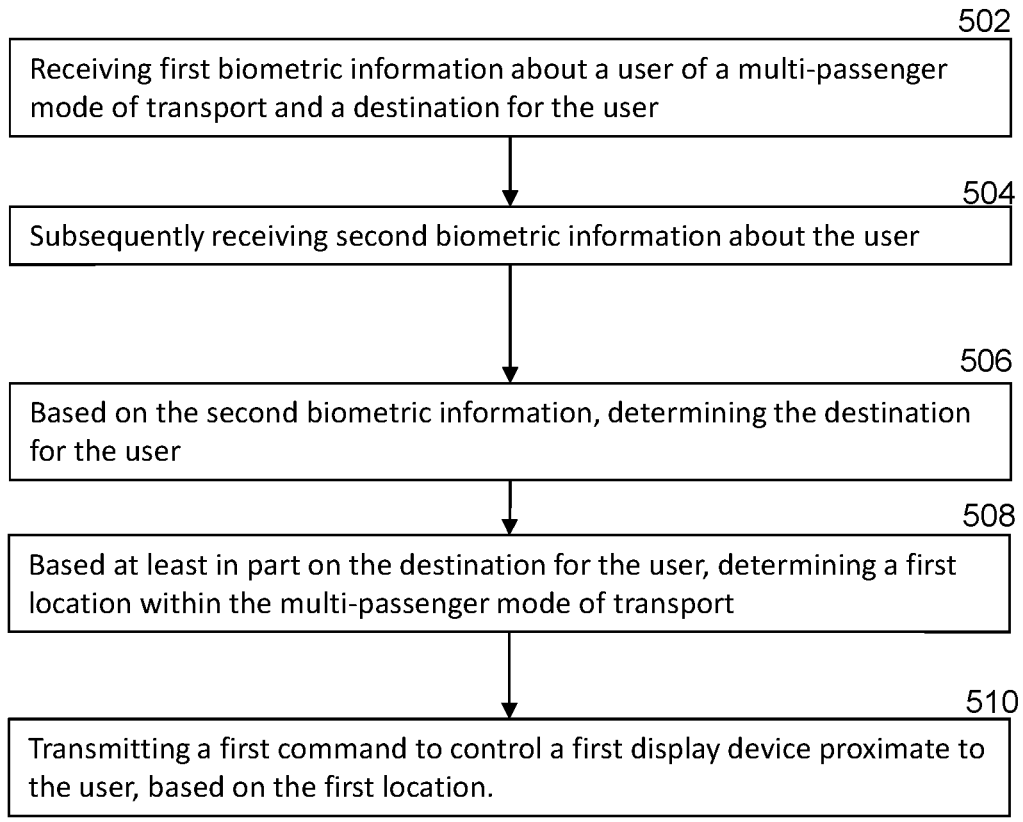
FIGS. 5A-5B are flowcharts illustrating example methods of providing an alert to a passenger based on a location of the passenger while in transit on a multi-passenger mode of transport, in accordance with the principles of the present disclosure.
Figure 5B:
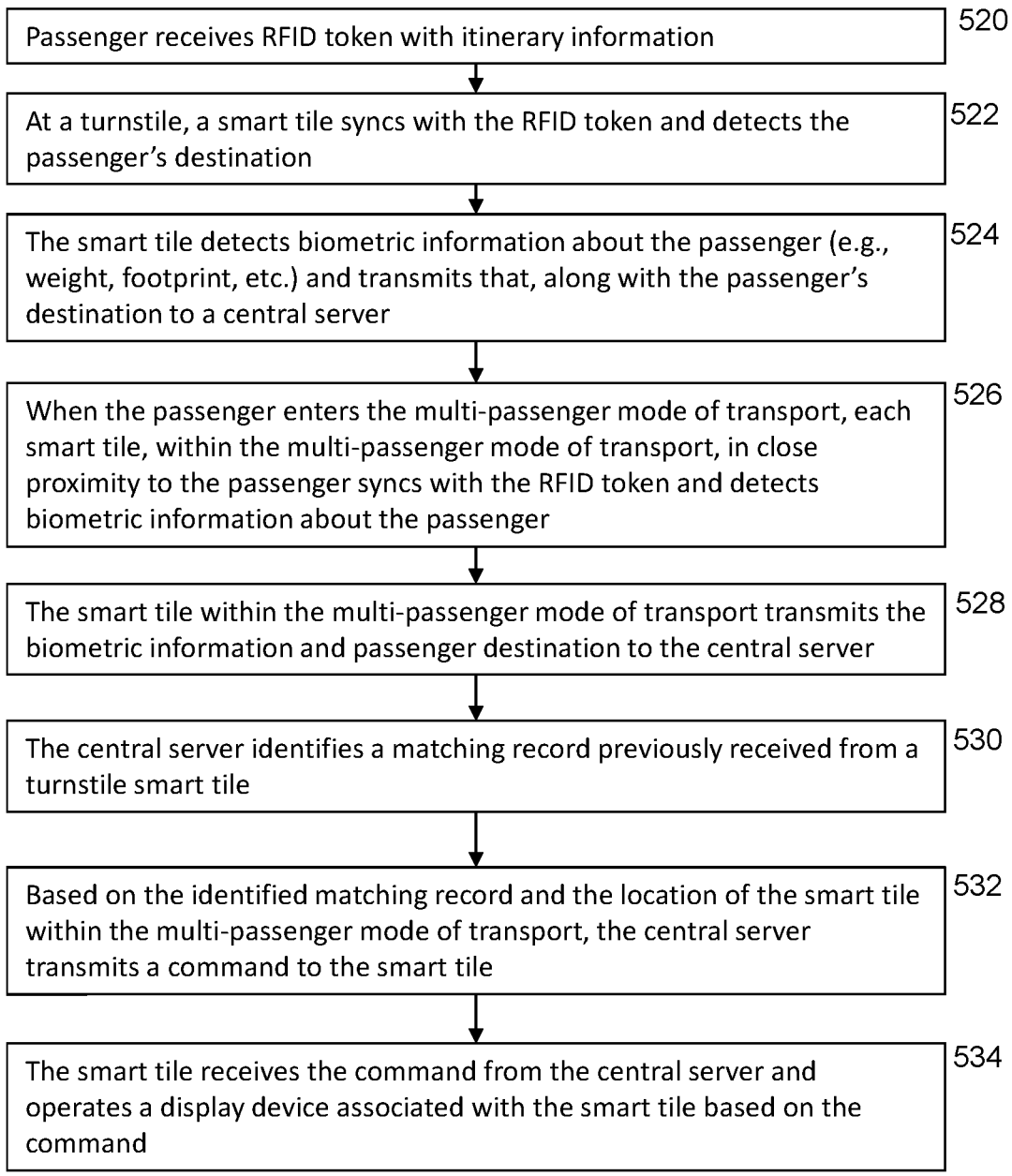

FIGS. 5A-5B are flowcharts illustrating example methods of providing an alert to a passenger based on a location of the passenger while in transit on a multi-passenger mode of transport, in accordance with the principles of the present disclosure.

In particular, FIG. 5A provides a brief description of embodiments of the present disclosure strictly from the viewpoint of the central system 111. FIG. 5B, however, provides a description of the interaction between the various systems and devices depicted in FIG. 1.

According to FIG. 5A, in step 502, the system 111 receives first biometric information about a user of a multi-passenger mode of transport (e.g., a train car) and a destination for that user. The first biometric information can, for example, be a weight and a footprint of a passenger. As mentioned above, the biometric information can be provided by a smart tile located at a turnstile. Along with the first biometric data, the smart tile may also transmit destination information associated with the passenger from which the first biometric information was detected. Subsequently, in step 504, the system 111 receives second biometric information about the user as well. As described above, this second biometric information can be provided by a second smart tile that is located on the floor of a train where the user stands. The second biometric data may also be a footprint of the user and their weight. This second smart tile may also interrogate nearby tokens to determine a destination associated with that token. At the time the second smart tile collects the second biometric data and the destination information, the second smart tile does not know for certain that the destination information is associated with the second biometric information. There may be a number of tokens close enough to interrogate, while there is only one set of second biometric information collected by the second smart tile.

The flowchart continues in step 506 with the system 111 determining, based on the second biometric information, the destination for the user. In one instance the system 111 can store the first biometric data and its associated destination as a record in a database. When the second biometric information is received by the system 111, the system 111 can query the database to find a matching set of biometric data. The system 111 could then extract the associated destination from the database record in order to determine the associated destination for that user. In an alternative, the system 111 can receive the second biometric information as well as destination information collected from a token. All three pieces of information could be used by the system 111 to identify a matching record in the database. In this way, if the system 111 receives a destination and second biometric data in which the biometric data matches a record but not its associated destination information, then the system 111 can determine that the second smart tile needs to interrogate a different, nearby token to find the token of the passenger that is actually standing on the second smart tile.

The system 111 continues, in step 508, by determining, based at least in part on the destination for the user, a first location within the multi-passenger mode of transport. As described above with respect to FIGS. 2A and 2B, the train car 200, 202 can be logically organized into separate regions and the separate regions being identified as appropriate or not appropriate areas or locations for the passenger to stand based on the passenger's destination. Thus, the system 111 can first determine what region in the train car is appropriate (or not appropriate) based on the passenger's destination relative to where the passenger embarks onto the train.

The flowchart of FIG. 5A concludes with step 510 with the system 111 transmitting a first command to control a first display device proximate to the user, based on the first location. The system 111 determines where in the train car the second biometric information is received from. For example, as described above, the system 111 may have foreknowledge of where each smart tile is located in the train car relative to an access point of the train car. Thus, each smart tile may have a unique identifier that allows the system 111 to determine a distance value, or simply a region of the train car, associated with the smart tile. Alternatively, the smart tile may have the distance value, or associated region information, stored therein and transmits this data to the system 111 along with the second biometric information. Accordingly, the system 111 can determine whether the second smart tile that collected the second biometric information is within the region of the train car identified as being appropriate. Based on whether or not the second smart tile is located in an appropriate region (i.e., the identified first location from step 508), the system 111 can send a command that instructs the second smart tile, or some other display device nearby, to glow a particular color (e.g., red, green, etc.).

The flowchart of FIG. 5B starts with step 520 in which a passenger receives an RFID token, or other NFC token, on which that passenger's itinerary information is stored. While a number of different pieces of data can be stored on the token, the data of interest in the present disclosure is the intended destination of the passenger. The passenger's departure location may also be used if relevant as the departure information and the destination information may be used by the system to determine how many stops are between the two locations. As mentioned above, this type of information can be used to identify an appropriate region within a train car for the passenger to stand or sit. The passenger may buy a ticket at a train station and be handed the token as part of the transaction. Alternatively, the passenger may buy a ticket from another location, or online, and be handed the token when the passenger redeems the ticket at the train station.

A first smart tile can be located at a turnstile that passengers use to gain access to trains at the train station such that when a passenger pauses at the turnstile to swipe the token on reader circuitry attached to the turnstile, the user steps onto the first smart tile. In step 522, the first smart tile and the token sync with one another so that the first smart tile can extract the passenger's destination (and possibly departure) information from the token. In step 524, the first smart tile also detects or collects first biometric information about the passenger standing on the first smart tile. The first smart tile transmits the passenger's itinerary information along with the associated first biometric data to the central system 111. The first biometric data can include a footprint outline and a weight for the passenger. At the central system 111, the first biometric information and its associated destination information are stored for later retrieval.

As described in step 526 of FIG. 5B, a passenger can enter a train car for example that has a number of smart tiles on the floor. One of these smart tiles in the train car is referred to below as "the second smart tile". The second smart tile collects second biometric information (e.g., a footprint, a weight) associated with a passenger standing on the second smart tile. Also, the second smart tile periodically scans its proximate area to determine whether or not any tokens are within range to successfully interrogate. The second smart tile syncs with a token and extracts the destination or any itinerary information from the token such that the destination information is associated with the second biometric information. As described above, there may be instances in which the second smart tile first determines which one token of a plurality of tokens within the train car is associated with the passenger standing on the smart tile.

According to step 528, the second smart tile transmits the second biometric information to the central system 111. The second smart tile may also transmit the destination information associated with the second biometric information to the central system 111. The central system 111, in step 530, identifies a first biometric information that matches the second biometric information. Because physical sensors may vary in calibration and sensitivity, the information may be considered to be matching if the difference between the information is within a predetermined threshold (e.g., less than 5%). The footprint outlines may be images and the system 111 can use known image analysis techniques to determine if one footprint outline matches the other. As one example, two or more key features of a footprint outline can be identified and their relative distances to one another can be used to determine matching footprint outlines. Alternatively, the footprint outline can be converted into a set of numerical data (e.g., a vertical length, a shortest horizontal width, and a largest horizontal width) that can be compared with similar data to identify matching footprint outlines.

In addition to identifying matching biometric data, the central system 111 may receive the associated destination information collected by the second smart tile. Thus, in almost every case, each passenger in a small area around a single smart tile can be uniquely identified by a record consisting of (footprint, weight, destination). In any case, the central system 111 can identify a destination associated with the passenger from which the second biometric data was collected.

Thus, in step 532, the central system can determine a command or instruction to send to the second smart tile. As discussed above, the train car can be broken into regions based on that region's distance from an access point of the train car. The central system 111 can determine which of the regions within the train car are appropriate for the different upcoming destinations of the train. The destination of the passenger from which the second smart tile collected the second biometric information is used to determine an appropriate region for that passenger. The central system 111 also uses location information of the second smart tile to determine whether or not the second smart tile is located within an appropriate region of the train car. Based on that latter determination, the central system 111 determines a command to send to the second smart tile to control a display device associated with the second smart tile.

Upon receiving the command from the central system 111, the second smart tile, in step 534, operates its associated display device to comply with the received command. As described above, the second smart tile can be instructed to emit one color to indicate to the passenger that they should move farther away from the access point and can be instructed to emit another color to indicate to the passenger that they are far enough from the access point based on their intended destination. In this way, the passenger can be provided an alert upon stopping at a location within the train car as to whether or not they should reconsider where they are located based upon the distance to their intended destination.

In addition to aspects of the present disclosure being useful for passengers of multi-passenger modes of transport, the same principles can be applied to elevators and similar environments in which smart tiles are used to construct the floor. Typically, in office buildings, the majority of people employed there have an identity badge or token that is used to gain access to different parts of the building or to pass through various security checkpoints. A server or other, similar system can be constructed that associates an RFID identifier on the badge or token with a floor of the building and possibly an elevator direction. For example, in the morning when an elevator is going up, an employee almost always exits the elevator on the $20^{th}$ floor. In the evening when the elevator is going down, the employee almost always exits at the $2^{nd}$ parking garage level. This information can be stored so that when that employee enters an elevator, the RFID identifier is detected by a sensor within the elevator and the difference between the starting floor and the ending floor is used to determine an appropriate region of the elevator at which the employee should stand. In this environment, the smart tiles do not need to collect biometric information or destination information and so all of the smart tiles can each light up in their correct color simply based on the destination floor associated with the employee. The employee can then easily move to an unoccupied area having the "green" color after entering the elevator.

Figure 6:
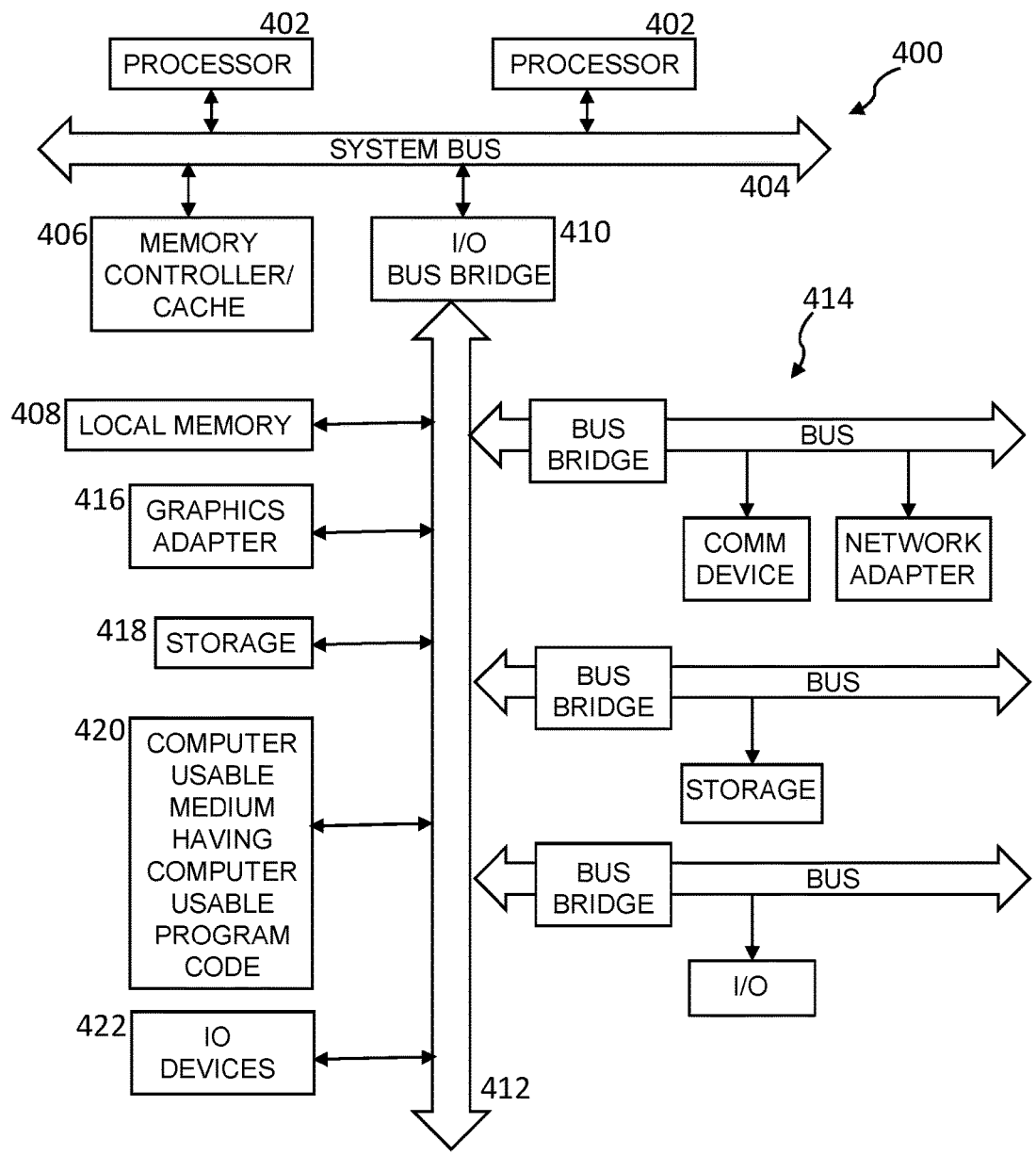
FIG. 6 depicts a block diagram of a data processing system in accordance with the present disclosure.

Referring to FIG. 6, a block diagram of a data processing system is depicted in accordance with the present disclosure. A data processing system 400, such as may be utilized to implement the hardware platform 111 or aspects thereof, e.g., as set out in greater detail in FIG. 1, may comprise a symmetric multiprocessor (SMP) system or other configuration including a plurality of processors 402 connected to system bus 404. Alternatively, a single processor 402 may be employed. Also connected to system bus 404 is memory controller/cache 406, which provides an interface to local memory 408. An I/O bridge 410 is connected to the system bus 404 and provides an interface to an I/O bus 412. The I/0 bus may be utilized to support one or more buses and corresponding devices 414, such as bus bridges, input output devices (I/O devices), storage, network adapters, etc. Network adapters may also be coupled to the system to enable the data processing system to become coupled to other data processing systems or remote printers or storage devices through intervening private or public networks.

Also connected to the I/O bus may be devices such as a graphics adapter 416, storage 418 and a computer usable storage medium 420 having computer usable program code embodied thereon. The computer usable program code may be executed to execute any aspect of the present disclosure, for example, to implement aspect of any of the methods, computer program products and/or system components illustrated in FIG. 1-FIG. 5B. It should be appreciated that the data processing system 400 can be implemented in the form of any system including a processor and memory that is capable of performing the functions and/or operations described within this specification. For example, the data processing system 400 can be implemented as a server, a plurality of communicatively linked servers, a workstation, a desktop computer, a mobile computer, a tablet computer, a laptop computer, a netbook computer, a smart phone, a personal digital assistant, a set-top box, a gaming device, a network appliance, and so on.

The data processing system 400, such as may also be utilized to implement the smart tile 450 or smart floor 244, or aspects thereof, e.g., as set out in greater detail in FIG. 4 and FIG. 2C respectively.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart(s) and block diagram(s) in the Figures illustrate the architecture, functionality, and operation of possible implementations of systems, methods, and computer program products according to various embodiments of the present invention. In this regard, each block in the flowchart(s) or block diagram(s) may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "includes," "including," "comprises," and/or "comprising," when used in this disclosure, specify the presence of stated features, integers, steps, operations, elements, and/or components, but do not preclude the presence or addition of one or more other features, integers, steps, operations, elements, components, and/or groups thereof.

Reference throughout this disclosure to "one embodiment," "an embodiment," "one arrangement," "an arrangement," "one aspect," "an aspect," or similar language means that a particular feature, structure, or characteristic described in connection with the embodiment is included in at least one embodiment described within this disclosure. Thus, appearances of the phrases "one embodiment," "an embodiment," "one arrangement," "an arrangement," "one aspect," "an aspect," and similar language throughout this disclosure may, but do not necessarily, all refer to the same embodiment.

The term "plurality," as used herein, is defined as two or more than two. The term "another," as used herein, is defined as at least a second or more. The term "coupled," as used herein, is defined as connected, whether directly without any intervening elements or indirectly with one or more intervening elements, unless otherwise indicated. Two elements also can be coupled mechanically, electrically, or communicatively linked through a communication channel, pathway, network, or system. The term "and/or" as used herein refers to and encompasses any and all possible combinations of one or more of the associated listed items. It will also be understood that, although the terms first, second, etc. may be used herein to describe various elements, these elements should not be limited by these terms, as these terms are only used to distinguish one element from another unless stated otherwise or the context indicates otherwise.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
    receiving, by a processor, first biometric information about a user of a multi-passenger mode of transport and a destination for the user;
    receiving, by the processor, second biometric information about the user;
    based on the second biometric information, determining, by the processor, the destination for the user;
    based at least in part on the destination for the user, determining, by the processor, a first location within the multi-passenger mode of transport; and transmitting, by the processor, a first command to control a first display device proximate to the user, based on the first location.

2. The computer-implemented method of claim 1, further comprising:
based at least in part on a physical location within the multi-passenger mode of transport where the second biometric information is collected, determining, by the processor, the first location within the multi-passenger mode of transport.

3. The computer-implemented method of claim 1, wherein determining the destination for the user comprises:
determining, by the processor that the first biometric data and second biometric data match.

4. The computer-implemented method of claim 1, wherein the first biometric data comprises one or more of a footprint and a weight.

5. The computer-implemented method of claim 1, wherein the second biometric data comprises one or more of a footprint and a weight.

6. The computer-implemented method of claim 1, further comprising:
calculating, by the processor, a distance from an access point of the multi-passenger mode of transport; and
based at least in part on the distance from the access point, determining, by the processor, the first location within the multi-passenger mode of transport.

7. The computer-implemented method of claim 1, wherein the first location comprises one of a plurality of adjacent zones within the multi-passenger mode of transport, each of the plurality of zones being a different, respective distance from an access point of the multi-passenger mode of transport.

8. The computer-implemented method of claim 1, wherein the first location comprises one of a plurality of tiles within the multi-passenger mode of transport, each of the plurality of tiles being a different, respective distance from an access point of the multi-passenger mode of transport.

9. The computer-implemented method of claim 1, further comprising:
receiving, by the processor, an indication that the multi-passenger mode of transport is closer to the destination than when the second biometric information was collected;
based at least in part on a current geographical location of the multi-passenger mode of transport, determining, by the processor, a second location within the multi-passenger mode of transport; and
transmitting, by the processor, the second location to a second display device proximate to the user.

10. The computer-implemented method of claim 9, wherein the second location is closer than the first location to an access point of the multi-passenger mode of transport.

11. A system, comprising:
a processor programmed to initiate executable operations comprising:
receiving first biometric information about a user of a multi-passenger mode of transport and a destination for the user;
receiving second biometric information about the user;
based on the second biometric information, determining the destination for the user;
based at least in part on the destination for the user, determining a first location within the multi-passenger mode of transport; and
transmitting a first command to control a first display device proximate to the user, based on the first location.

12. The system of claim 11, wherein the processor is programmed to initiate executable operations further comprising:
based at least in part on a physical location within the multi-passenger mode of transport where the second biometric information is collected, determining, by the processor, the first location within the multi-passenger mode of transport.

13. The system of claim 11, wherein the processor is programmed to initiate executable operations further comprising:
determining that the first biometric data and second biometric data match.

14. The system of claim 11, wherein the first biometric data comprises one or more of a footprint and a weight.

15. The system of claim 11, wherein the second biometric data comprises one or more of a footprint and a weight.

16. The system of claim 11, wherein the processor is programmed to initiate executable operations further comprising:
calculating a distance from an access point of the multi-passenger mode of transport; and
based at least in part on the distance from the access point, determining the first location within the multi-passenger mode of transport.

17. The system of claim 11, wherein the first location comprises one of a plurality of adjacent zones within the multi-passenger mode of transport, each of the plurality of zones being a different, respective distance from an access point of the multi-passenger mode of transport.

18. The system of claim 11, wherein the first location comprises one of a plurality of tiles within the multi-passenger mode of transport, each of the plurality of tiles being a different, respective distance from an access point of the multi-passenger mode of transport.

19. The system of claim 11, wherein the processor is programmed to initiate executable operations further comprising:
receiving an indication that the multi-passenger mode of transport is closer to the destination than when the second biometric information was collected;
based at least in part on a current geographical location of the multi-passenger mode of transport, determining a second location within the multi-passenger mode of transport; and
transmitting the second location to a second display device proximate to the user.

20. A computer program product, comprising:
a computer readable storage medium having program code stored thereon, the program code executable by a data processing system to initiate operations including:
receiving, by the data processing system, first biometric information about a user of a multi-passenger mode of transport and a destination for the user;
receiving, by the data processing system, second biometric information about the user;
based on the second biometric information, determining, by the data processing system, the destination for the user;
based at least in part on the destination for the user, determining, by the data processing system, a first location within the multi-passenger mode of transport; and transmitting, by the data processing system, a first command to control a first display device proximate to the user, based on the first location.

\* \* \* \* \*